United States Patent [19]

Foster et al.

[11] 4,003,952

[45] Jan. 18, 1977

[54] DIRECT HYDRATION OF OLEFINS TO ALCOHOLS

[75] Inventors: Elton Gordon Foster, Houston; Robert A. Golding, Missouri City; Delwin E. Dodd, Houston, all of Tex.

[73] Assignee: Shell Oil Company, Houston, Tex.

[22] Filed: Sept. 23, 1974

[21] Appl. No.: 508,030

[52] U.S. Cl. .......................... 260/641; 260/643 D; 23/270 R

[51] Int. Cl.$^2$ .................. C07C 29/04; C07C 29/24

[58] Field of Search .................. 260/643 D, 641

[56] References Cited

UNITED STATES PATENTS

| | | | |
|---|---|---|---|
| 2,044,414 | 6/1936 | Wilkinson | 260/643 D |
| 2,519,061 | 8/1950 | Mason | 260/641 X |
| 2,994,721 | 8/1961 | Wilson et al. | 260/641 X |
| 3,862,249 | 1/1975 | Ester et al. | 260/641 |

*Primary Examiner*—Bernard Helfin
*Assistant Examiner*—G. T. Breitenstein
*Attorney, Agent, or Firm*—Howard W. Haworth

[57] ABSTRACT

An improvement in the process for producing alcohols by the direct hydration of olefins in the presence of a catalyst, where the reactor effluent is scrubbed with water in a scrubbing zone and where the olefin feed is introduced in the lower portion of the scrubbing zone to strip out the organic impurities found in the aqueous alcohol product stream.

3 Claims, 1 Drawing Figure

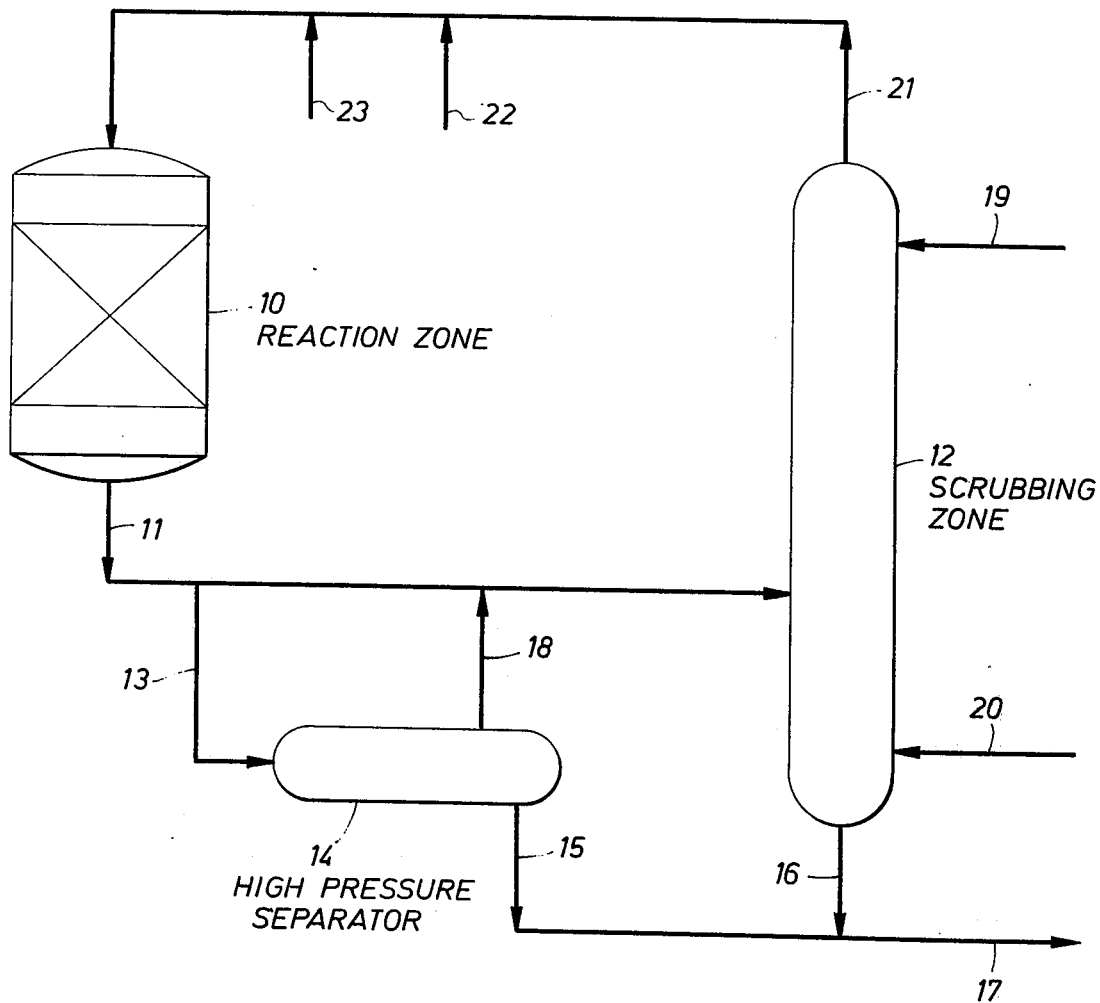

DIRECT HYDRATION OF OLEFINS TO ALCOHOLS

BACKGROUND OF THE INVENTION

1. Field of the Invention

Alcohols are conventionally produced by the direct vapor phase hydration of an olefin in the presence of a catalyst. The hydration reaction product contains the crude alcohol, unreacted olefin and by-product impurities. The reaction product is partially purified in a scrubbing zone wherein water is used to preferentially absorb the alcohol. The overhead from the scrubbing zone consists of unreacted olefin and most of the by-product impurities and is typically recycled to the reaction feed. The bottom stream from the scrubbing zone is the aqueous alcohol product which also contains a portion of the by-product impurities. This aqueous alcohol product is further processed in order to obtain a high purity alcohol product.

2. Description of the Prior Art

Alcohols are commercially synthesized by either the indirect hydration or direct hydration process. In a typical indirect process, the olefin is first absorbed in sulfuric acid; then, in a second step, water is added and an alcohol is formed. Direct hydration on the other hand is brought about by simultaneously contacting a solid or liquid catalyst with an olefin and water, thus producing alcohol in one step.

The principal use of the direct hydration method is the conversion of ethylene to ethanol. In one direct hydration process of the type described in U.S. Pat. Nos. 2,960,477 and Re 23,507, ethanol is produced at 540° F and 1000 psia by passing a gaseous mixture of recycle ethylene, fresh ethylene, and water through a catalyst bed of celite impregnated with phosphoric acid. About 4 to 5% of the ethylene in the feed stream is converted to alcohol on each pass, thereby requiring a large ethylene recycle stream. The reactor effluent is partially condensed, and the resultant gas phase is scrubbed with water in a recycle gas scrubber at high pressures wherein the remaining alcohol vapor is adsorbed in the water while most of the gaseous unconverted olefin and the ether by-product that is formed in the reactor is recycled back to the reactor. The combined dilute ethanol solution from the liquid phase of the scrubbing step and the partial condensate stream are concentrated by stripping with steam and then the concentrated ethanol solution is hydrogenated at low pressure to convert the small amount of aldehyde impurities to alcohol. Small quantities of ether and light ends in the ethanol solution are then removed as distillates. The ethanol solution is further processed in a final distillation step where an ethanol-water azeotrope (95 vol % ethanol) is separated as a highly purified side stream. The azeotrope can be used directly, offered for sale or dehydrated to 100 vol % ethanol.

Along with the hydration reaction of ethylene with water to form ethyl alcohol, numerous side reactions take place in the reactor. Among the many by-products formed in the reaction are diethyl ether, acetaldehyde, crotonaldehyde, and butyl alcohol. However, the principal by-product is diethyl ether comprising from 1 to 10% of the ethanol produced. The diethyl ether produced in the reactor is more volatile than the ethanol and has little commercial value. Since the ethylene conversion to both ethanol and diethyl ether is equilibrium limited, it is possible to reduce the net diethyl ether yield to near zero by recovering the diethyl ether from the ethanol product stream in downstream facilities and recycling the diethyl ether back to the reactor. In the usual process sequence, the ethanol is recovered from the reactor product vapor, which is mainly unreacted ethylene, by cooling and then scrubbing the reactor product vapors with water. During the scrubbing step, a portion of the diethyl ether is also scrubbed out with the ethanol and passes with the aqueous ethanol product from the bottom portion of the recycle gas scrubber to a final purification step. However, most of the diethyl ether from the reactor product vapors remains with the unconverted ethylene and is recycled from the top of the recycle gas scrubber to the reactor where the diethyl ether suppresses additional diethyl ether due to the equilibrium reaction mechanism. Although usually less than five percent of the diethyl ether in the reactor product stream is scrubbed out with ethanol, this amount of diethyl ether nevertheless constitutes a significant yield loss if not recycled.

Various methods for the purification of ethanol are known in the art. Carrier, U.S. Pat. No. 2,648,711 is concerned with the recovery of alcohol free of ether from olefin hydration products by injecting steam in the recycle gas scrubber as a stripping agent and by operating the recycle gas scrubber under the same conditions of temperature and pressure as found in the reactor, thereby removing the ether overhead from the recycle gas scrubber together with all the unreacted hydrocarbons and recovering the alcohol as an aqueous solution bottoms product from the recycle gas scrubber. The feed stream to the recycle gas scrubber in Carrier enters near the middle of the column. The bottoms from the recycle gas scrubber are then stripped with steam in a separate final stripping column and the purified alcohol is recovered as a top product. One variation on the Carrier process is presented in DeJean et al, U.S. Pat. No. 3,265,594, wherein the inventor employs an oil sidedraw on the final stripping column to remove inpurities. Another variation on the Carrier process is taught by Ester, U.S. Pat. No. 3,156,629, wherein the crude alcohol product stream from the reactor and an alkaline-aqueous stream are both introduced near the top of the recycle gas scrubber such that the impurities and unconverted olefin are withdrawn overhead while the purified aqueous alcohol bottom product is further processed in a second distillation column where the final alcohol product is withdrawn as a sidestream.

In addition to the straight distillation techniques as shown above, hydrogenation and inorganic chemical processes are also used to purify the alcohols. Nommenson et al, U.S. Pat. No. 2,944,087, teaches a combination distillation-hydrogenation technique to purify alcohol. In the Nommenson patent, the initial recycle gas scrubber and final stripping column steps are similar to those taught in the Carrier patent. However, Nommenson teaches the additional step of catalytic hydrogenation of the alcohol product stream from the final stripping column thereby improving the odor and permanganate time of the purified alcohol product. Maycock et al, U.S. Pat. No. Re 23,507, is concerned with controlling the pH of the reactor, particularly to reduce the formation of higher unsaturated aldehydes such as crotonaldehyde and sorbaldehyde. The Maycock purification process still requires the subsequent use of distillation techniques as taught in the Carrier, DeJean or Ester patents.

In the aforementioned patents, at least some of the impurities in the alcohol stream are removed in various steps outside the reaction system—the reaction system being defined as that part of the direct hydration process comprising the reactor vessel and the initial recycle gas scrubber plus the associated heaters, exchangers, pumps, compressors, flash vessels, and lines. However, it is more attractive and economical to perform this removal within the reaction system, especially where the crude alcohol taken as a bottoms stream from the recycle gas scrubber is used directly as a chemical intermediate and the normal distillation to high purity is not essential.

SUMMARY OF THE INVENTION

The present invention is an improvement in the process by which alcohol produced by the direct hydration of olefins is purified. The organic impurities produced in the reactor are removed within the reaction system and the crude aqueous alcohol stream taken from the bottom portion of the recycle gas scrubber may be used directly as a chemical intermediate without the necessity of further distillation to high purity. In particular, the invention is an improvement in the direct hydration process for the production of alcohols by reacting olefins with water in the presence of a catalyst whereby the alcohol along with a portion of the organic impurities produced as byproducts in the reaction zone are recovered from the effluent of the reaction zone in a scrubbing zone in which water is employed as a scrubbing agent. Specifically, the improvement comprises introducing the water near the top of the scrubbing zone and introducing the olefin makeup feed stream near the bottom of the scrubbing zone whereby the olefin feed stream acts as a stripping gas to strip the organic impurities from the alcohol stream product, thus producing an aqueous alcohol product with a reduced organic impurity content.

BRIEF DESCRIPTION OF THE DRAWING

The accompanying drawing diagrammatically illustrates the present invention. Shown therein is the reaction zone for conversion of the olefin to alcohol; a phase separator to separate out most of the water; and a recycle gas scrubbing zone to separate the alcohol from the unconverted olefin and impurities. For the most part, nonessential pieces of equipment, such as pumps, surge vessels, compressors, accumulators and the like, have been omitted for purposes of clarity.

DETAILED DESCRIPTION OF THE INVENTION

The process of the present invention while applicable to the recovery of ethers and other impurities associated with the production of various alcohols by the direct hydration of olefins, such as in the process to convert ethylene to ethanol and propylene to isopropanol, is particularly well suited for the recovery of diethyl ether in the direct hydration of ethylene to ethanol.

Whereas the prior art teaches methods for the recovery of diethyl ether in facilities downstream of the reaction system, the present invention performs the total diethyl ether recycle within the reaction system, thereby eliminating the need for additional processing equipment to purify the ethanol. This ability to recycle diethyl ether within the reaction system is especially desirable for any situation where crude ethanol, that is the ethanol stream leaving the reaction system prior to further purification, is used directly as a chemical intermediate and the usual distillation of the ethanol to high purity (95% vol plus) is not necessary.

This invention encompasses the addition of a multi-staged stripping section to the usual recycle gas scrubbing zone design wherein at least a portion of the fresh ethylene feed stream, normally routed directly to the reaction zone, is instead employed as a stripping gas in the recycle gas scrubber. In the invention, vapors from the reaction zone, containing ethanol, unconverted ethylene, water vapor, diethyl ether, and other impurities pass through a cooler and then to the recycle gas scrubbing zone, entering the scrubbing zone at some intermediate point. In a preferred embodiment, the cooled reaction product stream is first phase separated in a high pressure separator vessel where the condensed water and a portion of the ethanol are separated from the vapor stream. The uncondensed gases from the separator vessel, mostly ethylene with significant amounts of water vapor, ethanol and diethyl ether are further cooled before entering the scrubbing zone at an intermediate point. In the invention, a lean absorbent, for example, water, is injected near the top of the scrubbing zone and passes downward through the scrubbing zone to preferentially absorb the ethanol. However, the water as it passes downward through the scrubbing zone also absorbs a portion of the diethyl ether. In order to remove the diethyl ether from the aqueous ethanol product stream, the fresh ethylene stream is used as a stripping gas, entering the recycle gas scrubber near the bottom of the column and passing upflow countercurrent to the fat absorbent, thereby stripping the diethyl ether from the fat absorbent. The diethyl ether-rich stripping gas along with the unconverted ethylene and other gases not absorbed by the water are overheaded on the recycle gas scrubber and are recycled back to the reaction zone. The bottoms from the scrubbing zone which consists of an aqueous ethanol mixture with only trace amounts of diethyl ether is then combined with the condensed aqueous ethanol mixture from the high pressure separator vessel. This combined stream consisting of water and about 10 to about 40% vol ethanol, is then used directly as a chemical intermediate or else further purified to a higher concentration (e.g., 95% vol) through conventional means, such as distillation, hydrogenation or chemical treatment.

It is preferrable to use the entire amount of fresh ethylene as stripping gas. However, the invention does not preclude the splitting of the fresh ethylene stream with a portion of the ethylene being used as a stripping gas in the recycle gas scrubber and the remaining portion being routed directly to the reaction zone. The portion of the fresh ehtylene used as stripping gas is from about 25 to about 100%, preferably about 75 to about 100%. Such a splitting of the ethylene stream permits the added flexibility of controlling the diethyl ether content of the recycle gas scrubber bottoms stream at reasonable levels while reducing the amount of vapors that must be recycled back to the reaction zone.

DETAILED DESCRIPTION OF THE DRAWING

A fuller understanding of the present invention is obtained by reference to the accompanying drawing which reveals a preferred embodiment of the invention wherein the makeup ethylene stream is employed as the stripping gas in the direct hydration of ethylene to ethanol.

Referring to the drawing, ethylene reacts with water in the Reaction Zone 10 to form ethanol, diethyl ether, and other by-products. The converted ethanol, unconverted ethylene, water vapor, diethyl ether, and other reaction by-products pass from the Reaction Zone via line 11 to an intermediate point in the Scrubbing Zone 12.

An optional embodiment is also shown in the drawing. In this embodiment, all or a portion of the reaction product stream passes via lines 11 and 13 to a high pressure separator 14 where the condensed water and a portion of the ethanol are separated from the vapor stream and pass via line 15 to be combined with Scrubbing Zone bottoms product 16, thereby comprising the crude ethanol product 17 which is essentially free of any diethyl ether. The uncondensed gases, mostly ethylene with significant amounts of water, ethanol, and diethyl ether, leave the separator via line 18 and enter the Scrubbing Zone at an intermediate point.

A water stream is injected near the top of the Scrubbing Zone along line 19 to act as an absorbent and the fresh ethylene stream is injected through line 20 near the bottom of the Stripping Zone to act as a stripping gas. Typical Scrubbing Zone temperatures are about 150° F to about 300° F. The Scrubbing Zone is normally operated at about 700 to about 1200 psia.

The water injected along line 19 flows downward through the Scrubbing Zone, preferentially absorbing the ethanol while also absorbing some of the diethyl ether and exits the Scrubbing Zone through lines 16 and 17 as the crude ethanol product essentially free of diethyl ether. The makeup ethylene stream 20 injected near the bottom of the Scrubbing Zone, flows upward and exits the Scrubbing Zone through line 21 carrying with it most of the diethyl ether that would have remained with the aqueous ethanol product leaving the Scrubbing Zone through line 16.

The overhead from the Scrubbing Zone containing ethylene, water vapor, diethyl ether, and other impurities exits the Scrubbing Zone via line 21 and is contacted with water along line 22 before entering the Reaction Zone. In the alternative embodiment of the invention wherein the fresh makeup ethylene stream is split into two separate streams, the portion of the fresh ethylene not used as stripping gas is added to the combined Scrubbing Zone overhead stream and water stream via line 23 before entering the Reaction Zone.

ILLUSTRATIVE EMBODIMENT

The following illustrative embodiment reveals the superior results when the preferred embodiments of the invention as shown in the accompanying diagram are experimentally employed.

In an experiment, about 1100 to 1300 moles of Scrubbing Zone overhead are combined with makeup water and pass to the Reaction Zone. The overhead from the Scrubbing Zone contains about 800 to 1000 moles of ethylene, 70 to 100 moles of diethyl ether, with the remainder consisting of minor amounts of ethanol, water, and other organic compounds. In the Reaction Zone, the ethylene and water react in the presence of a phosphoric acid catalyst adsorbed on an inert carrier to form ethanol and diethyl ether. The bottom stream from the Reaction Zone is cooled and enters the Scrubber Zone at an intermediate point. Water is introduced near the top of the Scrubber Zone to act as an absorbent and about 100 moles of fresh ethylene makeup is injected near the bottom of the Scrubbing Zone to act as a stripping gas. The resultant crude ethanol product exits the Scrubbing Zone as the bottoms product stream and has a diethyl ether content of less than 0.02 mole % and an ethanol content of about 10 to 12 mole %.

COMPARATIVE EXAMPLE

The experiment described in the Illustrative Embodiment was repeated with the exception that the entire makeup ethylene stream was directly injected into the Reaction Zone along with the Scrubbing Zone overhead rather than injecting the makeup ethylene stream into the Scrubbing Zone directly. In addition, the bottoms from the Reaction Zone was injected into the Scrubbing Zone near the bottom of the Scrubbing Zone rather than at an intermediate point. The crude ethanol product leaving the Scrubbing Zone contained about 1 mole % ether and between 10 and 12 mole % ethanol.

We claim as our invention:

1. In the direct hydration process of producing ethanol by reaction ethylene with water in a reaction zone and in the presence of a catalyst whereby the ethanol along with a portion of the organic impurities produced as byproducts in the reaction including predominantly diethyl ether, are recovered from the effluent from said reaction zone in a scrubbing zone in which water is employed as a scrubbing agent, the improvement which comprises introducing said reaction zone effluent at an intermediate point in the scrubbing zone, introducing water near the top of the scrubbing zone, and introducing at least about 25% of the fresh ethylene feed stream near the bottom of the scrubbing zone, the ethylene thereby stripping the diethyl ether from the aqueous alcohol comprising the scrubber liquid bottom product and producing an aqueous alcohol product as scrubber liquid bottom product containing no more than trace amounts of diethyl ether.

2. The process as presented in claim 1 wherein at least a portion of the reaction zone effluent first passes through a separator to remove the condensed water and alcohol as a bottoms stream which is then combined with the scrubber liquid bottom product; and where the uncondensed gases overheaded in the separator are introduced at an intermediate point in the scrubbing zone.

3. The process as presented in claim 1 wherein from about 75 to about 100% of the fresh olefin feed is routed to the scrubbing zone as a stripping gas with the remainder of the fresh olefin feed routed to the reaction zone directly.

* * * * *